United States Patent
Li et al.

[11] Patent Number: 6,142,944
[45] Date of Patent: Nov. 7, 2000

[54] DOPPLER MOTION DETECTION WITH AUTOMATIC ANGLE CORRECTION

[75] Inventors: Pai-Chi Li; Tsung-Chun Cheng, both of Taipei, Taiwan

[73] Assignee: National Science Council of Republic of China, Taipei, Taiwan

[21] Appl. No.: 09/385,689

[22] Filed: Aug. 30, 1999

[51] Int. Cl.[7] .................................................... A61B 8/00
[52] U.S. Cl. .......................................................... 600/453
[58] Field of Search .................................. 600/443, 454, 600/455, 447, 453

[56] References Cited

U.S. PATENT DOCUMENTS

| | | | |
|---|---|---|---|
| 5,441,052 | 8/1995 | Miyajima | 600/455 |
| 5,910,119 | 6/1999 | Lin | 600/455 |
| 5,997,480 | 12/1999 | Sumanaweera et al. | 600/454 |

OTHER PUBLICATIONS

V.L. Newhouse, E.S. Furgason, G.F. Johnson. and D.A. Wolf, "The dependence of ultrasound bandwidth on beam geometry", IEEE Trans. on Sonics Ultrasonic, vol. SU–27, pp. 50–59, 1980.

P. Tortoli, G. Guidi, F. Guidi and C. Atenzi, "A review of experimental transverse Doppler studies", IEEE Trans. on Ultrason Ferroelec., Freq. Contr., vol. 41, pp. 84–89, 1994.

V.L. Newhouse, K.S. Dickerson, D. Cathiognol and J.Y. Chapelon, "Three–dimensional vector flow estimation using two transducers and spectral width", IEEE Trans. on Ultrason. Ferroelec., Freq. Contr., vol. 41, pp. 90–95, 1994.

G.E. Trahey, J.W. Allison and O.T. von Romm, "Angle independent ultrasonic detection of blood flow", IEEE Trans. on Biomed. Eng., vol. BME–34, pp. 965–967, 1987.

I.A Hein, "Triple–beam lens transducers for three–dimensional ultrasonic fluid flow estimation", IEEE Trans. on Ultrason. Ferroelec., Freq. Contr., vol. 42, pp. 854–869, 1995.

P.J. Phillips, A.P. Kadi and O.T. von Ramm, "Feasibility study for a two–dimensional diagnostic ultrasound velocity mapping system", Ultrasound Med. Biol., vol. 21, No. 2, pp. 217–229 1995.

C. Kasai, K. Namekawa, A. Koyano and R. Omoto, "Real–time two–dimensional blood flow imaging using an auto-correlation technique" IEEE Trans. Sonics Ultrason., vol. 32, No. 3, pp. 458–464, 1985.

S.M. Kay, Modern Spectral Estimation, Englewood Cliffs, N.J., Prentice Hall, 1988, Chaper 4.

*Primary Examiner*—Marvin M. Lateef
*Assistant Examiner*—Maulin Patel
*Attorney, Agent, or Firm*—Dougherty & Troxell

[57] ABSTRACT

Doppler principle has been widely applied to calculate the velocity of the object in motion. In medical ultrasonic imaging, it can be used to detect blood flow or myocardial motion. However, due to the inherent limitation of the Doppler effect, the measured velocity is only the projection of the actual velocity onto the ultrasound beam direction instead of the actual velocity. In previously proposed methods for measuring or correcting the Doppler angles, some need manual correction, others use complicated algorithms. They are either inconvenient to use or difficult to implement in current systems. In the method of Doppler motion detection with automatic angle correction according to the instant invention, it focuses on the relation between the Doppler angle and signal bandwidth to compute the Doppler angle by efficient correlation processing. Specifically, it uses variance of the Doppler signal to approximate square of the Doppler bandwidth. In addition, the actual velocity can be computed using the two-dimensional color mapping function existing in current color Doppler imaging systems. This method is not only suitable for efficient implementation, but also can be easily realized in current imaging systems to provide more accurate velocity information.

12 Claims, 6 Drawing Sheets

DOPPLER MOTION DETECTION WITH AUTOMATIC ANGLE CORRECTION

BACKGROUND OF THE INVENTION

1. Field of the Invention

This invention relates to Doppler motion detection with automatic angle correction and, in particular, to the calculation and display methods of Doppler angles. This method utilizes efficient correlation processing to compute the angle of motion and is applicable to real-time two-dimensional imaging. Using a two-dimensional mapping table, the method can be realized in current imaging systems.

2. Description of the Prior Art

Doppler effect is used to detect the velocity of motion from the frequency shift caused by the relative motion between two objects. In medical ultrasonic imaging, it is also widely used to compute the velocity of the blood flow or myocardial motion in human bodies, so it provides very important information for clinical diagnosis. However, the velocity measured by this method is the projection of the actual velocity onto the propagation direction of the sound waves. There will be no way to measure the real velocity and perform quantitative analysis without proper angle correction. To resolve this problem, current commercial systems rely on the operator to make the correction by marking the projection angle of the vessel displayed in the B-mode image. The main drawbacks of this type of methods are inconvenience and potential human errors. In contrast to the manual marking method, automatic measurement of Doppler angles has been proposed by various research groups. Although the basic principles of these methods are different, yet they all involve complicated calculations or need to significantly modify current system architectures. The present invention provides improvements over the previous methods.

SUMMARY OF THE INVENTION

The present invention provides a method of Doppler motion detection with automatic angle correction, through which the Doppler angle can be obtained from the efficient correlation processing based on the relation between the Doppler angle and the signal bandwidth. With the knowledge of Doppler angle, the actual velocity can be obtained. This method can be realized in current imaging systems to provide more accurate velocity information.

Another purpose of this invention is to provide an efficient method of automatic angle correction utilizing correlation functions in calculations. Without significantly changing the current software or hardware structures, the computation time can be greatly decreased.

Furthermore, the instant invention provides a method of automatic angle correction for Doppler velocity detection, which can be carried out in real-time two-dimensional imaging due to the dramatic decrease in computation time. Not only this method can be used in medical ultrasonic blood flow imaging, it is also applicable to myocardial tissue motion imaging and other Doppler measurements.

The automatic angle correction according to the invention with the above merits can be separated into the Doppler angle measurement and the velocity information display. As to the Doppler angle measurement, it takes the signal bandwidth and the relative position between the ultrasonic probe and the sample volume for calculation. In order to effectively compute the bandwidth, the instant invention abandons the traditional spectrum analysis method and makes use of correlation functions to speed up the calculation. Specifically, the present invention uses the variance of the Doppler signal to approximate square of the Doppler bandwidth. Since variance is routinely calculated in traditional color Doppler imaging systems, this invention can be readily carried out in current system structures without major modification. On the other hand, the present invention utilizes a simple one-dimensional or two-dimensional mapping table to determine Doppler angles and actual velocity. Velocity information can be displayed in colors or grey scale using this table.

BRIEF DESCRIPTION OF THE DRAWINGS

The drawings disclose an illustrative embodiment of the present invention which serves to exemplify the various advantages and objects hereof, and are as follows.

| | |
|---|---|
| 1 watertank | 10 Buffer |
| 11 high-pass filter | 12 Correlation function calculation |
| 13 average projected velocity | 14 Variance buffer |
| 15 temporal average | 16 spatial averaging |
| 17 two-dimensional mapping | 18 Display |
| 2 string phantom | 21 pulley 1 |
| 22 pulley 2 | 23 pulley 3 |
| 24 String | 3 DC motor |
| 4 doppler angle | 5 Transducer |
| 6 pulser/receiver | 7 Arbitrary waveform generator |
| 8 A/D converter | 9 storage and signal analysis |

DETAILED DESCRIPTION OF THE PREFERRED EMBODIMENT

1. Principle

Figure 1:
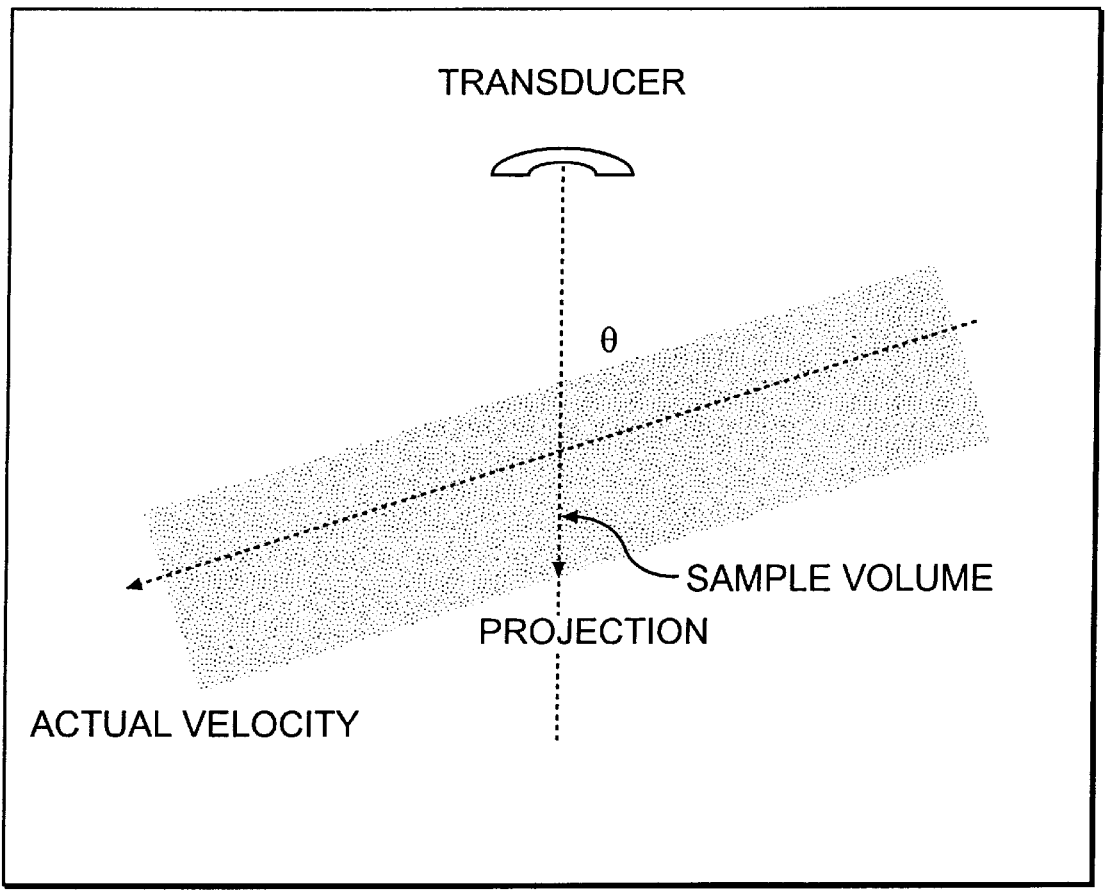
FIG. 1 is an illustrative diagram of the projection of the actual motion velocity in the detection direction measured base on the Doppler principle according to the present invention.

The velocity of motion measured by the Doppler principle is the projection of the actual velocity in the ultrasound beam direction (please refer to FIG. 1, which is an illustrative diagram of the projection of the actual velocity in the detection direction). However, conventional Doppler methods can not obtain the velocity projected onto the direction perpendicular to the beam direction. In order to resolve this issue, many research groups have proposed angle measurement and correction methods [1–6]. Reference [1] proposed a method to obtain this perpendicular component by the Doppler bandwidth. The main principle is shown in FIG. 1. Since each sample volume is a three dimensional region with a finite size, thus when the scatterer passes through the volume, different positions in the same sample volume result in different projection angles and produce the Doppler bandwidth. The Doppler bandwidth is inversely proportional to the time interval for the object in motion to pass through the sample volume (i.e. transit time) [1].

The relation between the Doppler bandwidth (bw) and the angle can be expressed as $$bw \approx k \cdot \frac{v \cdot \sin\theta}{w},$$

where v is the actual flow velocity, θ is the Doppler angle, w is the width of the sample volume, and k is a constant determined by bw and w. Because the velocity obtained from the traditional Doppler measurement is the projection of the actual velocity in the ultrasound beam direction, i.e., v·cos θ, the angle could be determined by $$\theta = \tan^{-1}\left(\frac{bw \cdot w}{k \cdot v \cdot \cos\theta}\right).$$

2. Fast calculation of the bandwidth by correlation processing

The bandwidth can be directly measured from the Doppler spectrum. However, it needs a longer computation time and is only applicable to spectral Doppler measurements. Therefore, it is not suitable for real-time two-dimensional imaging. The method according to the invention uses correlation functions to calculate the bandwidth. Since this type of calculation needs a shorter computation time and correlation processing has been routinely implemented in current color Doppler imaging systems, this method can realize real-time two-dimensional blood flow imaging without significantly affecting current system architectures.

Variance of the Doppler signal is used to approximate square of the Doppler bandwidth. Suppose P(ω) is the Doppler power spectrum, then the variance is defined as $$\text{variance} = \frac{\int_{-\infty}^{\infty}(\omega - \bar{\omega})^2 P(\omega) d\omega}{\int_{-\infty}^{\infty} P(\omega) d\omega}.$$

If P(ω) is Gaussian distributed and $\sigma_\omega$ is the Doppler bandwidth, then P(ω) can be written as $$P(\omega) = e^{-\pi\left(\frac{\omega - \bar{\omega}}{\sigma_\omega}\right)^2}.$$

Combine the above equations, one can find that the variance of the velocity is proportional to the square of the bandwidth, that is, $$\text{variance} = \frac{\sigma_\omega^2}{2\pi}.$$

When the Doppler power spectrum is not Gaussian, even though an analytic expression of the bandwidth in terms of the variance is not easy to obtain, the variance is still approximately proportional to the square of the bandwidth.

The method of calculating the variance using correlation functions can be found in reference [7]. If S(t) is the Doppler signal received by the imaging system, the autocorrelation function R(t) can be defined as $$R(t) \equiv \int_{-\infty}^{\infty} S^*(t+\tau)S(\tau) d\tau.$$

Since P(ω) is the Fourier transform of R(t), the Doppler frequency shift corresponding to the projection of the average projected velocity is [7]

$$\bar{\omega} = \frac{\int_{-\infty}^{\infty} \omega P(\omega) d\omega}{\int_{-\infty}^{\infty} P(\omega) d\omega} = -j\frac{R'(0)}{R(0)}.$$

Furthermore, from the previous definition of the variance one can obtain $$\text{variance} \approx \frac{2}{T^2}\left[1 - \frac{|R(T)|}{R(0)}\right].$$

Therefore, the bandwidth can be calculated from R(0) and R(T).

In practice, the correlation function is a discrete function and is calculated within a finite time. Suppose T is the time interval between two successive pulses, i.e., the pulse repetition interval, if the number of sample points is N, R(0) and R(T) are expressed as $$\hat{R}(0) = \frac{1}{N}\sum_{i=1}^{N} S^*(i \cdot T)S(i \cdot T),$$

$$\hat{R}(T) = \frac{1}{N-1}\sum_{i=1}^{N-1} S^*((i+1) \cdot T)S(i \cdot T).$$

The number of sample points affects the accuracy of the correlation function. Since a negative variance might occur with these formulas [8], one may use a modified formula to obtain R(0):

$$\hat{R}(0) = \frac{1}{2(N-1)}\sum_{i=1}^{N-1}[|S(i \cdot T)|^2 + |S((i+1) \cdot T)|^2].$$

3. The relation between the variance and the Doppler angle

Please refer to FIG. 1 as an illustration of the ultrasonic blood flow imaging system, the angle between the blood flow and the sound wave propagation direction, θ, is the projection angle. Using simulations based on the parameters listed in table1, one is able to find the relation between the angle and the variance. Color Doppler typically takes 4 to 12 samples. This is far less than the situation in spectral Doppler typically where 32 to 128 samples are used. Therefore, larger errors occur. To decrease the errors, temporal or spatial averaging of the variance can be used. The temporal average is the average variance over time in a specific sample volume, namely, $$\overline{\text{variance}_t} = \frac{1}{M}\sum_{i=1}^{M} \text{variance}(x_0, y_0, t_i),$$

where $x_0$ and $y_0$ are spatial coordinates, $t_i$ is the time instance, and $\overline{variance}_i$ is the temporal average. The spatial average is the average variance over neighboring points in a one- or two-dimensional image, that is, $$\overline{variance}_s = \frac{1}{M}\sum_{i=1}^{M} variance(x_i, y_i, t_0),$$

where $\overline{variance}_s$ is the spatial average.

TABLE 1

| Speed of sound | 1540 m/s. |
|---|---|
| Pulse repetition frequency | 10 kHz |
| Center frequency | 5 MHz |
| Number of the scatterer | Single |
| Width of the probe | 1 cm |
| Focus of the probe | 2 cm |

Figure 2:
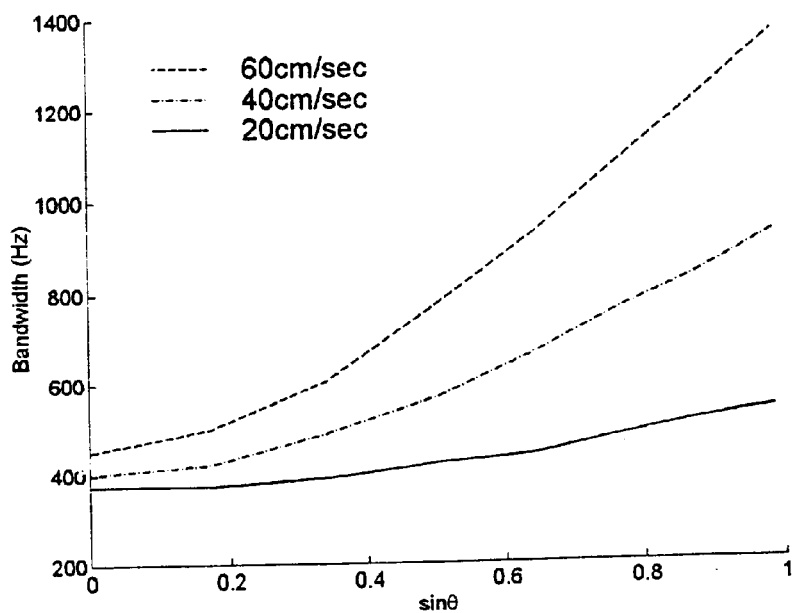
FIG. 2 shows the relation between the Doppler bandwidth and the velocity of the scattering object according to the invention.

FIG. 2 shows the relation between the Doppler bandwidth and the velocity of the scatterer. The length-to-width ratio of the sample volume is set to 5 while the three curves correspond to the scatterer velocity (from top to bottom) for 60 cm/sec, 40 cm/sec and 20 cm/sec, respectively.

Figure 3:
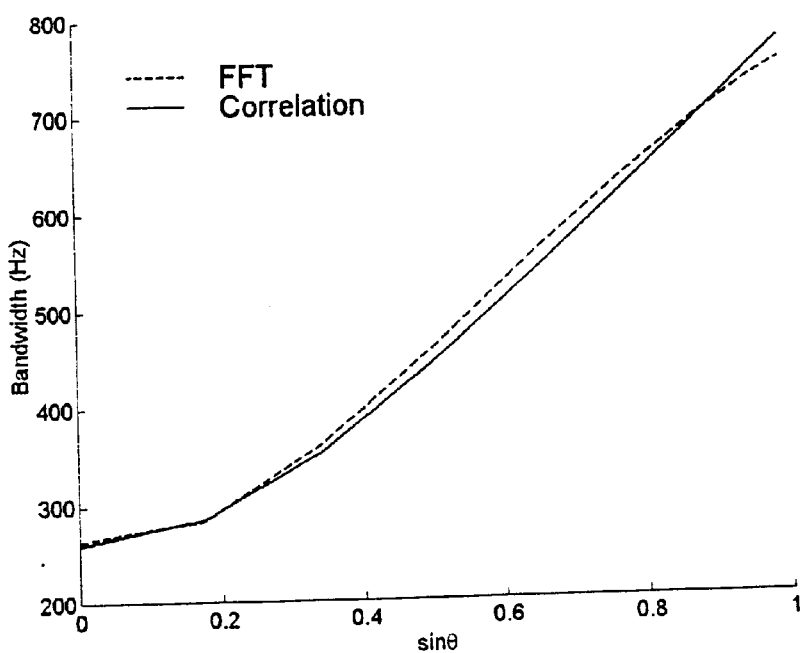
FIG. 3 is a diagram which compares the correlation method and the FFT method.

Please refer to FIG. 3, which is a diagram that compares the correlation method to the FFT (Fast Fourier Transformation) method. In this figure, the dashed line represents the −6.82 dB bandwidth using FFT, while the solid line is the bandwidth calculated by the variance, i.e., bw=$\sqrt{2\pi}\sigma$. The number of samples in both cases is 64. In spite that the Doppler power spectrum is not Gaussian, the bandwidth derived from the variance still reasonably represents the actual bandwidth.

Figure 4:
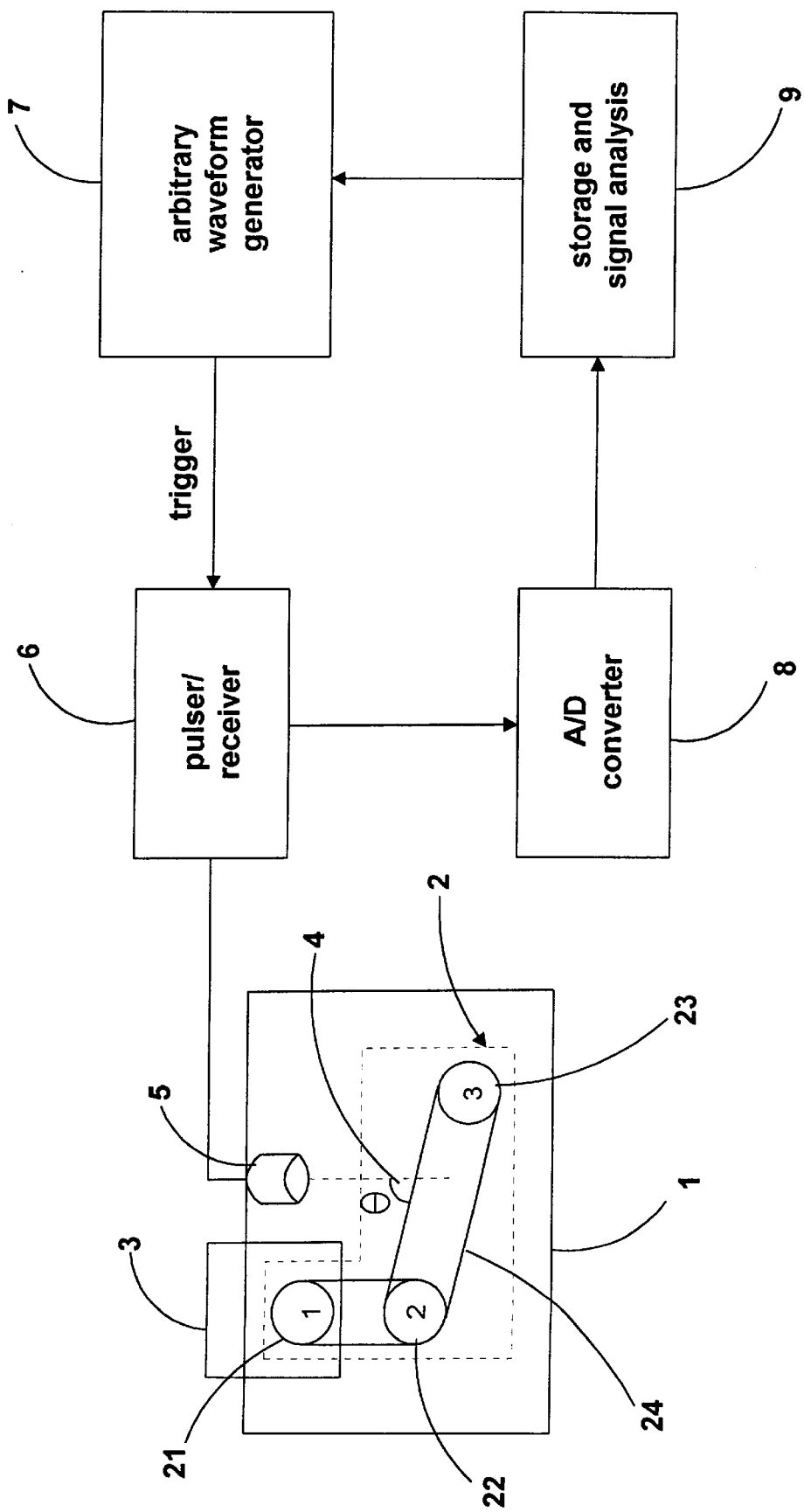
FIG. 4 is the block diagram of the experimental system for automatic angle correction.

FIG. 4 shows the experimental system block diagram for Doppler angle correction. The backscattered signal is generated by a Doppler string phantom 2. Pulley 1 (21) of the string phantom 2 in the water tank 1 is driven by a DC motor 3. The string 24 connecting pulleys 2 and 3 (22,23) is then driven. The Doppler signal is generated by the motion of the thin rope 24 connecting pulleys 2 and 3 (22 and 23). The Doppler angle θ 4 is the angle between the thin rope 24 and the direction of the sound wave. This angle 4 can be adjusted by changing the positions of pulleys 2 and 3 (22 and 23). The purpose of using the string phantom 2 is for accurate control of the speed and the angle 4. Therefore, it is suitable for verifying the method according to the instant invention.

The center frequency of the transducer 5 is 5 MHz. The transmit signal of the transducer 5 is generated by a pulser, whose trigger signal and pulse repetition frequency are controlled by an arbitrary waveform generator 7 according to the image depth and the speed of the string. After being amplified by a receiver 6, the received signals are sampled by an A/D converter for Doppler signal analysis 9.

Figure 5:
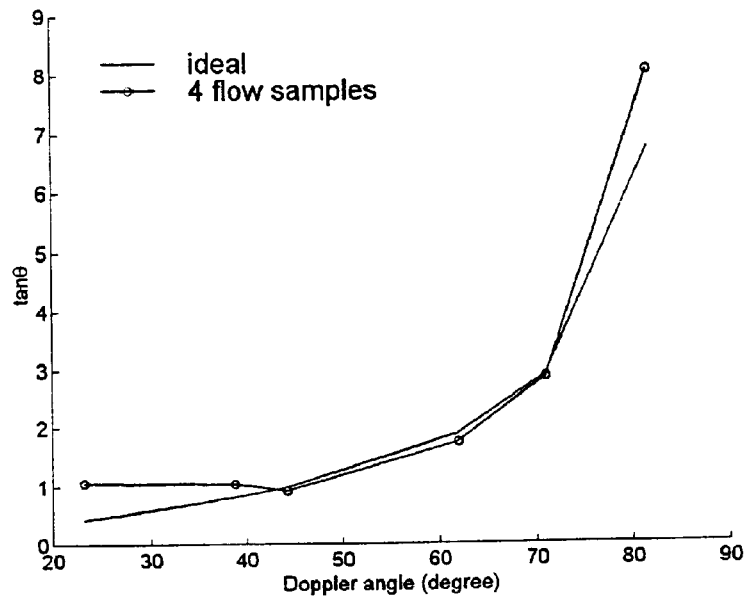
FIG. 5 shows the experimental results of the automatic angle correction for Doppler velocity detection.
Figure 6:
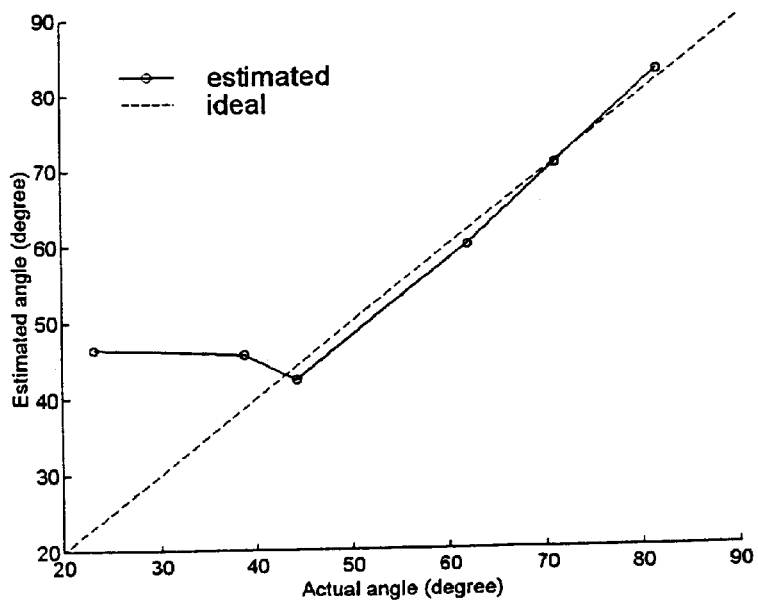
FIG. 6 is for additional experimental results of the automatic angle correction for Doppler velocity detection.

With the above experimental set-up and by adjusting the positions of pulleys 2 and 3 (22,23), signals at Doppler angles 23°, 39°, 44°, 62°, 71°, and 82° are measured. The actual string speed (without projection) is around 35 cm/sec and the receive gate length is 7.5 mm. Therefore the length-to-width ratio of the sample volume is about 7.5. The string speed at different angles has minor variations and must be corrected. One advantage of this method is that calculation of the Doppler angle is independent of the velocity. FIG. 5 shows experimental results of the automatic angle correction method using the correlation method. The line with circles represents tangent of the estimated angles and the solid line represents ideal values. Four flow samples are used and each variance value is averaged over nine points (continuous 36 samples for 9 variance values). The k value is 11. It is seen that the error between the experimental values and actual values is larger at small angles. This inaccuracy in calculation is due to the insufficient observation time. In other words, the bandwidth is not determined by the transit time in this case. It is determined by the number of flow samples times pulse repetition interval. FIG. 6 plots the same results as in FIG. 5 with the change in the vertical axis to be the estimated angle. One can still see, except for small angles, the consistency between experimental results and actual values.

Figure 7:
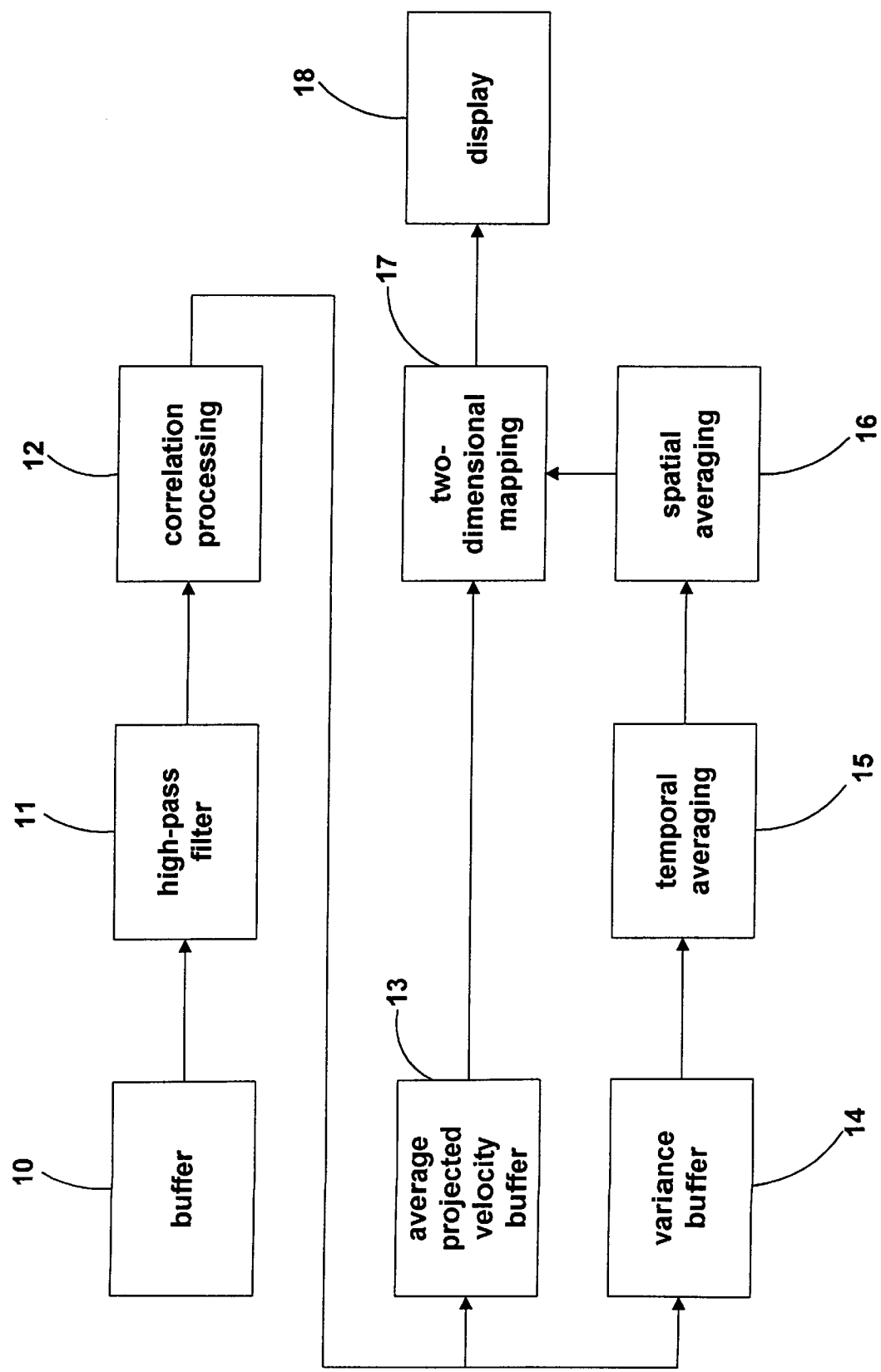
FIG. 7 is a system block diagram of the automatic angle correction method for Doppler velocity detection.

Please refer to FIG. 7, which is a system block diagram of a potential implementation of the invention. This diagram shows that after the image signal output by a buffer 10 passes a high-pass filter 11 to remove the signals from stationary objects, the system performs the correlation processing 12. The average projected velocity and the variance from the calculation are stored in an average projection velocity buffer 13 and a variance buffer 14, respectively, prior to temporal averaging 15 and spatial averaging 16. The variance buffer 14 is also used to guarantee the synchronization among signals. Finally, the speed is determined by a two-dimensional mapping 17. The final image can be output to a display device 18 in grey scale or colors.

The two-dimensional map can realize an arbitrary function with the projected velocity speed and the variance as the input parameters, that is, $$output(R,G,B)=f(\overline{\omega}, \overline{variance})$$

where $f(\cdot)$ is the arbitrary function, (R,G,B) represents the output colors, and $\overline{variance}$ is the temporal or spatial average or a combination of both.

Figure 8:
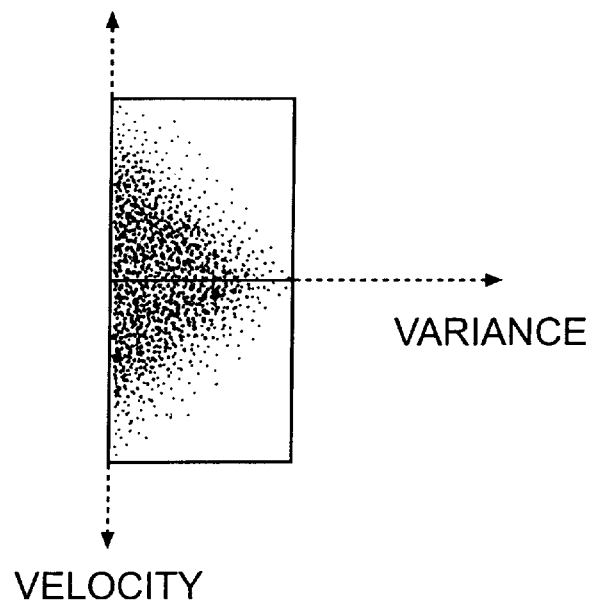
FIG. 8 is a diagram, with the velocity as the vertical axis while the variance as the horizontal axis, of the automatic angle correction method for Doppler velocity detection.

FIG. 8 is a potential mapping scheme of the automatic angle correction method, with the velocity as the vertical axis and the variance as the horizontal axis. The map can be designed such that, at the same actual velocity, one can use the same color for display.

Figure 9:
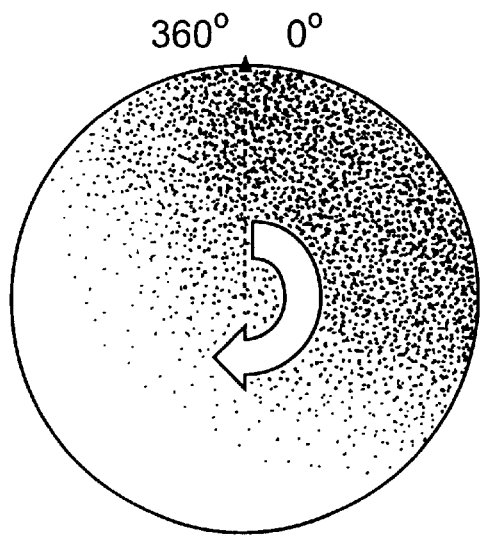
FIG. 9 is an illustrative diagram of another mapping scheme.

FIG. 9, describes another potential mapping scheme. One can see in this figure that the blood flow direction can be shown in the range from 0° to 360° and each direction is represented by a unique color.

Compared with other prior arts, Doppler motion detection with automatic angle correction according to the present invention has the following merits:

1. The method of the present invention calculates the Doppler angle by efficient correlation processing based on the relation between the Doppler angle and the Doppler bandwidth. Not only is this method efficient, but it can also be realized in current imaging systems to provide more accurate velocity information.
2. The invention utilizes variance to approximate square of the Doppler bandwidth. Without significantly changing the software or hardware structures of current systems, variance can be efficiently implemented and processed. The instant invention provides a method for Doppler motion detection with automatic angle correction, which can be carried out in real-time two-dimensional imaging due to the significant decrease in processing time. This method can provide more accurate clinical information. It can not only be used in medical ultrasonic blood flow imaging, but is also applicable to myocardial tissue imaging and other Doppler measurements.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A method of Doppler motion detection with automatic angle correction of an imaging system, the method comprising:

measuring automatically the velocity and direction of motion of an image object by the Doppler principle, wherein said imaging system further comprises correlation processing based on the relation between the Doppler angle and the Doppler bandwidth and using variance to approximate the square of the Doppler bandwidth for measuring the angle of motion, and correcting and displaying the velocity of the image object.

2. A method of Doppler motion detection with automatic angle correction as in claim 1, wherein the image data of said imaging system can be retrieved from a ultrasonic transducer and system, said image object can be blood flow or human tissues in motion, and the velocity and direction of motion of said object can be displayed with other stationary objects in the same area in grey scale or colors at the same time.

3. A method of Doppler motion detection with automatic angle correction as in claim 1, wherein the velocity and angle of motion of said imaging system are obtained by a correlation function method.

4. A method of Doppler motion detection with automatic angle correction according to claim 3 wherein said angle of motion is calculated by a variance computed from the correlation function and the correspondence between said variance and said angle can be looked up in a mapping table.

5. A method of automatic angle correction via Doppler velocity detection as in claim 3, wherein said variance of said correlation function method can be a temporal average, a spatial average (one- or two-dimensional), or a proper combination of both the temporal and spatial averages.

6. A method of Doppler motion detection with automatic angle correction, wherein the angle correction is based on the average projected velocity and variance.

7. A method of Doppler motion detection with automatic angle correction as in claim 6, wherein said angle correction is implemented by a two-dimensional mapping table.

8. A display of Doppler motion detection with automatic angle correction, the method comprising the steps of:

measuring automatically the velocity and direction of motion of an image object by the Doppler principle, wherein said imaging system further comprises correlation processing based on the relation between the Doppler angle and the Doppler bandwidth and using variance to approximate the signal of the Doppler bandwidth for measuring the angle of motion, and correcting and displaying the velocity of the image object; and showing the angle of motion or corrected actual velocity in gray scale or colors.

9. A method of Doppler motion detection with automatic angle correction according to claim 8 wherein said display method includes the step of determining average projected velocity and simultaneously relates said average projected velocity and angle to different color displays by a two-dimensional mapping table, and said two-dimensional mapping table can be constructed based on any function with required inputs.

10. A method of Doppler motion detection with automatic angle correction as in claim 8, wherein said display method makes automatic correction to the angles by a two-dimensional mapping table so that the same velocity is represented by the same color and said velocity information can be independently displayed by texts or diagrams.

11. A method of Doppler motion detection with automatic angle correction as in claim 8, wherein said display method makes use of a two-dimensional mapping table so that the same velocity is represented by the same color and said velocity information can be independently displayed by texts or diagrams.

12. A method of Doppler motion detection with automatic angle correction as in claim 8, wherein said display method makes automatic correction to the angles by a two-dimensional mapping table so that different angles and velocities are expressed by different colors and said velocity information can be independently displayed by texts or diagrams.

* * * * *